US012774401B2

(12) United States Patent
Kong et al.

(10) Patent No.: US 12,774,401 B2
(45) Date of Patent: Oct. 27, 2026

(54) TEMPERATURE-SENSITIVE ADHESIVE FOR STOMA, AND ADHESIVE TAPE FOR STOMA COMPRISING SAME

(71) Applicant: Korea Institute of Science and Technology, Seoul (KR)

(72) Inventors: Hosung Kong, Seoul (KR); Hung Gu Han, Seoul (KR); Sook Lee, Pyeongtaek-si (KR); Edward SH Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 509 days.

(21) Appl. No.: 18/547,964

(22) PCT Filed: Feb. 28, 2022

(86) PCT No.: PCT/KR2022/095042

§ 371 (c)(1),
(2) Date: Aug. 25, 2023

(87) PCT Pub. No.: WO2022/197168

PCT Pub. Date: Sep. 22, 2022

(65) Prior Publication Data

US 2024/0182754 A1 Jun. 6, 2024

(30) Foreign Application Priority Data

Mar. 19, 2021 (KR) ........................ 10-2021-0035867

(51) Int. Cl.
*C09J 7/35* (2018.01)
*A61F 5/443* (2006.01)
(Continued)

(52) U.S. Cl.
CPC ................ *C09J 7/35* (2018.01); *A61F 5/443* (2013.01); *A61L 24/0089* (2013.01);
(Continued)

(58) Field of Classification Search
None
See application file for complete search history.

(56) References Cited

U.S. PATENT DOCUMENTS 4,680,333 A * 7/1987 Davis ..................... C08K 5/098 525/333.1
2005/0214352 A1 9/2005 Hori et al.
(Continued)

FOREIGN PATENT DOCUMENTS

CA 2902145 A1 * 10/2014
JP 3935582 B2 * 6/2007
(Continued)

OTHER PUBLICATIONS 2-page brochure for Technomelt PS 1540 by Technomelt, Downloaded on May 22, 2026.*
(Continued)

*Primary Examiner* — Tae H Yoon
(74) *Attorney, Agent, or Firm* — NSIP Law

(57) ABSTRACT

The present invention relates to an adhesive for a stoma and an adhesive tape for a stoma comprising the same. Specifically, the present invention relates to: an adhesive for a stoma, which can be attached to an affected part, having high adhesion, and has improved functionality for easy detachment from the skin; and an adhesive tape for a stoma comprising the same.

10 Claims, 1 Drawing Sheet

(51) Int. Cl.

| | |
|---|---|
| ***A61L 24/00*** | (2006.01) |
| ***A61L 24/06*** | (2006.01) |
| ***C09J 125/06*** | (2006.01) |

(52) U.S. Cl.

CPC ............. *A61L 24/06* (2013.01); *C09J 125/06* (2013.01); *A61L 2300/22* (2013.01); *A61L 2300/224* (2013.01); *C09J 2301/122* (2020.08); *C09J 2301/304* (2020.08); *C09J 2400/16* (2013.01); *C09J 2401/00* (2013.01); *C09J 2425/00* (2013.01)

(56) References Cited

U.S. PATENT DOCUMENTS

| | | | | |
|---|---|---|---|---|
| 2007/0077422 | A1 | 4/2007 | Ishiwatari et al. | |
| 2020/0001579 | A1* | 1/2020 | Hirose .................... | B32B 27/32 |

FOREIGN PATENT DOCUMENTS

| | | | | |
|---|---|---|---|---|
| JP | 2010-012506 | A | | 1/2010 |
| JP | 2010-265375 | A | | 11/2010 |
| JP | 2011-006352 | A | | 1/2011 |
| JP | 2011-052056 | A | | 3/2011 |
| JP | 2011-072437 | A | | 4/2011 |
| JP | 2011-126864 | A | | 6/2011 |
| KR | 102079911 | B1 | * | 2/2020 |

OTHER PUBLICATIONS

Extended European Search Report issued on Dec. 16, 2024 in counterpart European Patent Application No. 22771834.3. (7 pages in English).

* cited by examiner

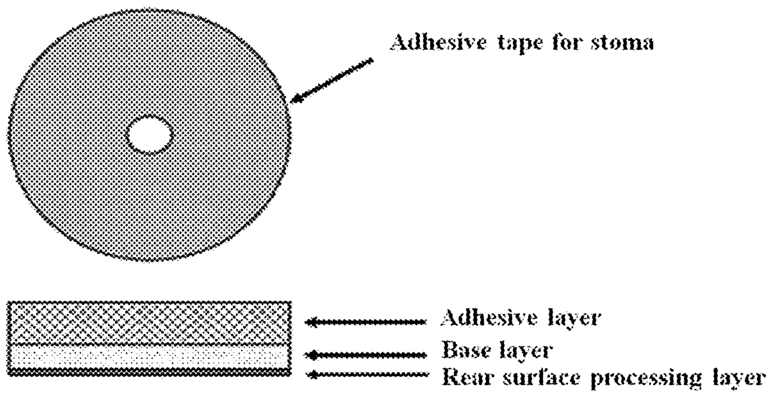
Adhesive tape for stoma
Adhesive layer
Base layer
Rear surface processing layer

TEMPERATURE-SENSITIVE ADHESIVE FOR STOMA, AND ADHESIVE TAPE FOR STOMA COMPRISING SAME

CROSS-REFERENCE TO RELATED APPLICATIONS

This application is a U.S. national stage application of International Application No. PCT/KR2022/095042 filed on Feb. 28, 2022, which claims the benefit of Korean Patent Application No. 10-2021-0035867 filed on Mar. 19, 2021, in the Korean Intellectual Property Office, the entire disclosures of which are incorporated herein by reference for all purposes.

TECHNICAL FIELD

The present invention relates to a temperature-sensitive adhesive for a stoma and an adhesive tape for a stoma including the same.

BACKGROUND ART

As one of the medical adhesive tapes, an adhesive tape for a stoma is commonly used in the form of a thin circular tape having a hole in the center, as shown in FIG. 1.

An adhesive refers to an adhesive that may attach an object to a surface of another object with a low pressure in a short time without any driving force such as water, a solvent, light, heat, and the like, and may also easily detach the attached object without contamination of the object when the attached object is detached. In this case, the adhesive may include in a basic configuration: elastomeric materials having adhesion, such as rubbers, acryls, silicones, and the like; coagulants serving to enhance a cohesion property, such as acrylic acid, styrene monomers, and the like; functional radicals imparting various functionalities, for example, improving a cross-linking property, enhancing water solubility and absorbency, and the like; and tackifiers such as rosins, terpenes, and the like. Meanwhile, because respective elements which determine the adhesion of the adhesive as described above have a characteristic of being inversely proportional to each other, the elements should be appropriately blended so that their contents can be optimized in order to prepare an adhesive suitable for the purpose of use.

The adhesive includes an acrylic resin, or the like as a basic raw material, and solvent-type adhesives that use a solvent such as toluene have the longest history for general industries and precision industries. However, because the medical adhesives should not be fundamentally harmful to the human body and also meet the international requirements for medical supplies, such as by the FDA, water-soluble adhesives in which water is used as the solvent, or solvent-free adhesives such as hot-melt adhesives have been increasingly used recently. The hot-melt adhesives may be mainly classified into thermoplastic resins including ethylene-vinyl acetate-based resins, such as ethylene-vinyl acetate-based resins in which a tackifying resin, a plasticizing oil, and the like are blended into a copolymer of a polystyrene block and a polybutadiene and polyisoprene block; and polyurethane-based thermosetting resins. Also, cyanoacrylate as a quick-drying glue and a fibrin glue as a bio-adhesive are attracting worldwide attention, both of which are medical adhesive materials used clinically as adhesives for surgical sutures.

However, the adhesive has contradictory requirements that it should fundamentally maintain strong adhesion to a surface of an adherend when it is attached to the adherend, but have a property of being detached when it is detached from the adherend. In particular, in the case of medical adhesives, there are problems to be solved, such as various types of medical adhesive-related skin injuries (MARSI) caused when the adhesive is detached (Wounds UK, Vol. 12, Issue 4, November 2016). Specifically, an adhesive tape used in ostomy bags has a problem in that skin rashes caused by the frequent attachment/detachment of the adhesive aggravate pain because most patients live with a ostomy bag for the rest of their lives. In Korea, over 220,000 patients have used the ostomy bag, and worldwide, approximately 3 million patients also have used the ostomy bag. Therefore, this problem needs to be definitely solved all over the world.

Meanwhile, as a method of easily detaching an adhesive from a surface of an adherend, Japanese Patent Laid-Open Publication No. 2010-265375 discloses a method of using a thermal foam, Japanese Patent Laid-Open Publication No. 2010-012506 discloses a method of irradiating a photoinitiator and ultraviolet rays, and Japanese Patent Laid-Open Publication No. 2011-052056 discloses a method of using electricity. However, the above-described methods are suitable for dissolving adhesives used for industrial purposes, but are not suitable for use for medical purposes. For example, as disclosed in Japanese Patent Laid-Open Publication No. 2010-265375, when the adhesive is heated at a temperature of 120° C. for approximately 5 minutes, adhesion may decrease by approximately 90% when compared to room temperature. Accordingly, this method cannot be applied to the human body.

In recent years, regarding medical adhesives, an adhesive for attachment to the skin which consists of a polyisocyanate compound and an acrylic acid alkyl ester copolymer having no carboxyl and hydroxyl groups and containing an N-vinyl cyclic lactam (Japanese Patent Laid-Open Publication No. 2011-006352), an adhesive consisting of a copolymer of N-hydroxyalkylacrylamide and an acrylic acid alkyl ester having no carboxyl group (Japanese Patent Laid-Open Publication No. 2011-126864), an addition-curable adhesive composition including a polyoxyalkylene polymer as a main component (Japanese Patent Laid-Open Publication No. 2011-072437), and the like have been disclosed. However, such adhesives may reduce the force used when they are detached from the skin, but consequently, because the adhesive force of the adhesive is weakened, they are not suitable as an adhesive for a stoma primarily requiring solid adhesion to the patient's skin for a predetermined period of time.

Also, as an adhesive for a stoma, registered Korean Patent No. 10-2079911 discloses a composition designed to facilitate the detachment from the skin by blending a carboxy-modified styrene-butadiene-based rubber resin into an acrylic polymeric resin matrix to impart functionality so that adhesion can decrease at a low temperature (0° C.). However, the composition is not so suitable for use for medical purposes because it is a solvent-type adhesive.

Therefore, there is a need for a medical adhesive having improved functionality to facilitate the detachment from the skin, more particularly, a solvent-free adhesive (such as a water-soluble adhesive or a hot-melt adhesive) which has strong adhesion to the skin when an adhesive for a stoma is attached to the skin, and also may be easily detached from the skin without any skin troubles when the detachment from the skin is required.

DISCLOSURE

Technical Problem

The present invention provides an adhesive for a stoma, which has high adhesion to the skin when it is attached to the skin, and is easily detached from the skin when it is peeled off, and an adhesive tape for a stoma including the same. Specifically, the present invention relates to an adhesive for a stoma, which may be attached to an affected part with high adhesion and has improved functionality to facilitate the detachment from the skin under an optional condition of a low temperature of approximately 0° C. to 5° C., and an adhesive tape for a stoma including the same. The present specification is not limited to the objective described above, and other objectives which have not been described will be clearly understood by those of ordinary skill in the art from the following description.

These and other objects and advantages of the present invention will be understood by the following detailed description. It is also to be easily understood that the objects and advantages of the present invention can be realized by the means or methods described in the claims, and a combination thereof.

Technical Solution

One embodiment of the present invention provides an adhesive for a stoma, which includes a thermoplastic hot-melt resin and a fatty acid metal salt, wherein the adhesion reduction rate ΔF defined by the following General Formula 1 is at least 50%:

[General Formula 1]

$$\Delta F = \frac{(\text{Room-temperature adhesion} - \text{Low-temperature adhesion})}{\text{Room-temperature adhesion}} \times 100$$

wherein:

the room temperature adhesion is a value measured at 23° C. according to ASTM D3330, and the low temperature adhesion is a value measured at 0° C. according to ASTM D3330.

Another embodiment of the present invention provides an adhesive tape for a stoma, which includes a base layer; an adhesive layer provided on one surface of the base layer, wherein the adhesive layer includes the above-described adhesive for a stoma.

Advantageous Effects

An adhesive for a stoma according to one embodiment of the present invention includes a thermoplastic hot-melt resin and a fatty acid metal salt together, and thus has advantages in that it has excellent adhesion to the skin, and also serves to facilitate the detachment from the skin due to its very low adhesion during low temperature treatment.

Since the adhesive for a stoma according to one embodiment of the present invention has a very high adhesion reduction rate due to the internal cohesion of the adhesive by creating a low temperature atmosphere during the detachment from the skin, it has an advantage of minimizing the occurrence of skin troubles in patients.

These and other effects and advantages of the present invention will be more clearly understood by the following detailed description of the present invention, the claims, and the accompanying drawings.

DESCRIPTION OF DRAWINGS

FIG. 1 shows a structure of a conventional adhesive tape for a stoma.

BEST MODE

Throughout the specification, unless explicitly stated otherwise, the term "comprise" will be understood to mean the inclusion of stated elements without excluding any other elements.

Throughout the specification, when an element is located "on" another element, this includes not only when one element is in contact with another element but also when another element is present between the two elements.

Hereinafter, the present invention will be described in detail. In this case, the terms and words used in the present specification and the claims should not be interpreted as being limited to typical meanings or dictionary definitions, but should be interpreted as having meanings and concepts relevant to the technical scope of the present invention based on the principle that an inventor can appropriately define the concepts of terms to describe his/her invention in the best way. Therefore, the embodiments described in this specification and the configurations shown in the drawings of the present invention are merely the most preferred embodiments but do not represent all of the technical spirit of the present invention. Thus, the present invention should be construed as including all the changes, equivalents, and substitutions included in the spirit and scope of the present invention at the time of filing this application.

The present inventors have made continuous research on an adhesive for a stoma having improved functionality to facilitate the detachment from the skin, and found that, when a thermoplastic hot-melt resin and a fatty acid metal salt (R—COO-M wherein R—COO represents a fatty acid, and M represents a metal) are applied to the adhesive for a stoma at the same time as in the present invention, the adhesive for a stoma may be easily attached to an affected part with high adhesion, and may be easily detached from the skin. Therefore, the present invention has been completed based on the above facts. Specifically, the adhesive for a stoma according to the present invention may be easily detached from the skin due to a significant decrease in adhesion of the adhesive itself when the adhesive is optionally exposed to a low temperature atmosphere at the point of time when the detachment is required, and the adhesion of the adhesive may return to its original level when the temperature increases to room temperature.

As an adhesive for a stoma, one embodiment of the present invention provides an adhesive for a stoma, which includes a thermoplastic hot-melt resin and a fatty acid metal salt, wherein the adhesion reduction rate ΔF defined by the following General Formula 1 is at least 50%:

[General Formula 1]

$$\Delta F = \frac{(\text{Room-temperature adhesion} - \text{Low-temperature adhesion})}{\text{Room-temperature adhesion}} \times 100$$

wherein:

the room temperature adhesion is a value measured at 23° C. according to ASTM D3330, and the low temperature adhesion is a value measured at 0° C. according to ASTM D3330.

As described above, since the adhesive for a stoma according to the present invention has a significant difference between adhesion at room temperature (23° C.) and adhesion at a low temperature (0° C.), it may maintain high adhesion to an affected part when it is attached to the affected part, and conversely, may be easily detached by selectively creating a low temperature atmosphere during the detachment from the affected part.

According to one embodiment of the present invention, the adhesion reduction rate may be at least 50%, at least 70%, at least 80%, or at least 85%.

The adhesive for a stoma according to the present invention has advantages such as highly excellent adhesion even at room temperature. Therefore, the adhesive for a stoma according to the present invention may be attached to the skin with high adhesion to prevent foreign substances from escaping to the outside when the adhesive for a stoma is applied to ostomy bags.

According to one embodiment of the present invention, the room temperature adhesion of the adhesive for a stoma may be at least 10 N/25 mm. Specifically, the room temperature adhesion of the adhesive for a stoma may be at least 15 N/25 mm, or at least 20 N/25 mm. Also, when the adhesive for a stoma includes heat transfer particles, the room temperature adhesion may be at least 40 N/25 mm, at least 50 N/25 mm, or 60 N/25 mm.

According to one embodiment of the present invention, the fatty acid metal salt may be dispersed in a polymeric matrix derived from the thermoplastic hot-melt resin. Specifically, the adhesive for a stoma may be in the form in which the thermoplastic hot-melt resin and the fatty acid metal salt are physicochemically bonded to each other. To prepare such an adhesive for a stoma, a method of physically mixing the thermoplastic hot-melt resin and the fatty acid metal salt may be used.

Also, according to one embodiment of the present invention, the adhesive for a stoma may include a composite polymeric matrix of the thermoplastic hot-melt resin and the fatty acid metal salt. Specifically, the adhesive for a stoma may include a composite polymeric matrix obtained through the physicochemical bonding of the thermoplastic hot-melt resin and the fatty acid metal salt. To prepare such an adhesive for a stoma, a method of mixing one or more thermoplastic hot-melt resins and fatty acid metal salts having functional groups capable of being cross-linked with the thermoplastic hot-melt resins may be used.

According to one embodiment of the present invention, the thermoplastic hot-melt resin may have a glass transition temperature Tg of −10° C. to 30° C. When the glass transition temperature of the thermoplastic hot-melt resin is greater than room temperature, specifically 30° C., the adhesive for a stoma becomes too hard at room temperature. On the other hand, when the glass transition temperature is less than −10° C., the adhesive has a poor effect of reducing adhesion in a low temperature (0° C.) atmosphere. Accordingly, the glass transition temperature of the thermoplastic hot-melt resin in the present invention is most preferably in a range of 0° C. to 30° C., or in a range of 0° C. to room temperature.

According to one embodiment of the present invention, the thermoplastic hot-melt resin may include at least one selected from the group consisting of an ethylene vinyl acetate-based hot-melt resin, a polyethylene-based hot-melt resin, a polypropylene-based hot-melt resin, a polyester-based hot-melt resin, a styrene-based hot-melt resin, a polyamide-based hot-melt resin, and a polyurethane-based hot-melt resin. Specifically, the thermoplastic hot-melt resin may be a styrene-based hot-melt resin, for example, a hot-melt resin from the Technomelt PS series (commercially available from Henkel AG & Co. KGaA). In this case, hot-melt resins known in the art, which fall within the above-described range of glass transition temperature, may be used, but the present invention is not limited thereto.

According to one embodiment of the present invention, the fatty acid metal salt may be derived from a fatty acid selected from caprylic acid ($C_8H_{16}O_2$), lauric acid ($C_{12}H_{24}O_2$), myristic acid ($C_{14}H_{28}O_2$), palmitic acid ($C_{16}H_{32}O_2$), stearic acid ($C_{18}H_{36}O_2$), linolenic acid ($C_{18}H_{30}O_2$), arachidonic acid ($C_{20}H_{32}O_2$), oleic acid ($C_{18}H_{34}O_2$); and a metal selected from lithium (Li), aluminum (Al), calcium (Ca), magnesium (Mg), potassium (K), zinc (Zn), and sodium (Na). Specifically, the fatty acid in the fatty acid metal salt may be derived from a saturated fatty acid selected from caprylic acid ($C_8H_{16}O_2$), lauric acid ($C_{12}H_{24}O_2$), myristic acid ($C_{14}H_{28}O_2$), palmitic acid ($C_{16}H_{32}O_2$), and stearic acid ($C_{18}H_{36}O_2$); or an unsaturated fatty acid selected from linolenic acid ($C_{18}H_{30}O_2$), arachidonic acid ($C_{20}H_{32}O_2$), oleic acid ($C_{18}H_{34}O_2$). Also, the metal in the fatty acid metal salt may be derived from a metal selected from lithium (Li), aluminum (Al), calcium (Ca), magnesium (Mg), potassium (K), zinc (Zn), and sodium (Na). That is, the fatty acid metal salt may be a compound in which the metal is bound to the above-described saturated or unsaturated fatty acid. For example, the fatty acid metal salt may be zinc stearate. The fatty acid metal salt may physically/chemically react with a functional group, which affects the adhesion of a polymeric matrix derived from the thermoplastic hot-melt resin, to greatly reduce the adhesion of the adhesive for a stoma.

According to one embodiment of the present invention, the content of the fatty acid metal salt may be 10 parts by weight or more and 30 parts by weight or less, based on 100 parts by weight of the thermoplastic hot-melt resin. Specifically, the content of the fatty acid metal salt may be 15 parts by weight or more and 20 parts by weight or less, based on 100 parts by weight of the thermoplastic hot-melt resin. When the content of the fatty acid metal salt falls within the above range, the adhesive for a stoma may significantly enhance adhesion at room temperature, and may also realize a very large drop in adhesion at a low temperature so that the adhesive for a stoma can be easily detached from the skin. Specifically, when the content of the fatty acid metal salt exceeds the above range, the content of the thermoplastic hot-melt resin may be relatively reduced, resulting in degraded room temperature adhesion, and the adhesive for a stoma may irritate the skin to cause erythema. Also, when the content of the fatty acid metal salt is less than the above range, a decrease in adhesion at a low temperature may not occur sufficiently due to the excessively low content of the fatty acid metal salt.

According to one embodiment of the present invention, the adhesive for a stoma may further include at least type of heat transfer particle selected from the group consisting of metal particles, ceramic particles, and carbon particles. The heat transfer particles may increase a heat transfer rate in the adhesive for a stoma to cause adhesion to decrease more rapidly during the detachment of the adhesive for a stoma.

The metal particles may be metal particles including a metal selected from the group consisting of iron (Fe), aluminum (Al), copper (Cu), gold (Au), silver (Ag), and magnesium (Mg), or alloy particles including the same. Also, the ceramic particles may be ceramic particles including at least one selected from the group consisting of beryllium oxide (BeO), boron nitride (BN), aluminum nitride (AlN), silicon carbide (SiC), silicon nitride ($Si_3N_4$), and alumina ($Al_2O_3$). In addition, the carbon particles may be carbon particles including at least one selected from the group consisting of graphene, carbon nanotubes, exfoliated graphite, and carbon.

According to one embodiment of the present invention, the heat transfer particles may have an average diameter of 1 μm to 100 μm, preferably 5 μm to 20 μm. When the average diameter of the heat transfer particles is less than 1 μm, the heat transfer particles have a problem in that it is difficult to have an effect on the heat transfer rate. On the other hand, when the average diameter of the heat transfer particles is greater than 100 μm, the bonding of materials may become weak, or the adhesion to the adherend may become poor.

According to one embodiment of the present invention, the content of the heat transfer particles may be in a range of 10 parts by weight to 200 parts by weight, based on 100 parts by weight of the thermoplastic hot-melt resin. Specifically, the content of the heat transfer particles may be in a range of 50 parts by weight to 200 parts by weight, 100 parts by weight to 200 parts by weight, or 150 parts by weight to 200 parts by weight, based on 100 parts by weight of the thermoplastic hot-melt resin. Within the above content range of the heat transfer particles, an effect of the heat transfer particles on the adhesion of the adhesive for a stoma may be minimized, and the adhesion reduction rate in a low temperature atmosphere may be maximized.

According to one embodiment of the present invention, the adhesive for a stoma may further include one or more additives selected from the group consisting of a coagulant, an absorbent, a tackifier, an antioxidant, a dispersion stabilizing agent, a coupling agent, a thickening agent, and a drying control agent.

The coagulant may include at least one selected from acrylic acid, methacrylic acid, vinyl acetate, and a styrene monomer, and may be added to adjust the cohesive strength of the adhesive for a stoma.

The absorbent may include at least one selected from sodium carboxymethyl cellulose, sodium polyacrylate, methylcelluse, polyvinyl alcohol, and may absorb moisture from the skin during the attachment of the adhesive for a stoma to prevent a decrease in the adhesion of the adhesive for a stoma.

The tackifier may include at least one selected from a hydrogenated rosin resin, a hydrogenated and esterified rosin resin, a hydrogenated terpene resin, and a petroleum resin, and may be added to adjust the adhesive strength and initial wettability of the adhesive for a stoma.

The content of the additive may be properly adjusted within a range that does not deteriorate the characteristics of the adhesive for a stoma.

One embodiment of the present invention provides an adhesive tape for a stoma, which includes a base layer; and an adhesive layer provided on one surface of the base layer, wherein the adhesive layer includes the above-described adhesive for a stoma.

The base layer may be a polyester film such as a polyethylene naphthalate (PEN) film, a poly(ethylene terephthalate) (PET) film, a poly(butylene terephthalate) (PBT) film, or a polycarbonate (PC) film; a polyolefin film such as a polypropylene (PP) film, a polyethylene (PE) film, or a cycloolefin film (COP); a polyether ether ketone (PEEK) film, or an acryl film. In this case, base layers (or base films) used in the art may be applied, but the present invention is not limited thereto.

According to one embodiment of the present invention, the base layer may further include at least one type of heat transfer particle selected from the group consisting of metal particles, ceramic particles, and carbon particles. The heat transfer particles may be the same as the heat transfer particles included in the adhesive for a stoma as described above.

According to one embodiment of the present invention, the adhesive for a stoma may further include a rear surface treatment layer formed on the other surface of the base layer. The rear surface treatment layer may be a layer subjected to various rear surface treatment processes applied in the art. The rear surface treatment layer may further include the above-described heat transfer particles as in the base layer.

The content of the heat transfer particles may be in a range of 0.1 parts by weight to 50 parts by weight, based on 100 parts by weight of the base layer or rear surface treatment layer. However, the present invention is not limited thereto, and the content of the heat transfer particles may be properly adjusted within a range that does not deteriorate the performance of the base layer or the rear surface treatment layer.

To create a low temperature atmosphere during the detachment of the adhesive tape for a stoma attached to the skin, the heat transfer particles may cause a rapid temperature drop of the adhesive layer to effectively induce the cohesion of the adhesive layer when a volatile substance such as a rubbing alcohol is applied on the skin, or the skin comes into contact with an ice bag. In particular, when rubbing alcohol is sprayed during the detachment of the adhesive tape for a stoma, the rubbing alcohol has advantages in that it may penetrate into the capillary structure in the adhesive tape for a stoma to reduce adhesion, may induce the cohesion of the adhesive layer due to the temperature drop by volatilization, and may also sterilize an affected part.

MODE FOR INVENTION

Hereinafter, examples of the present invention will be described in detail to help the understanding of the present invention. However, it should be understood that the examples according to the present invention can be modified in many different ways, and the scope of the invention should not be construed as limited to the following examples. Thus, the examples of the present invention are provided to more fully describe the present invention to those skilled in the art.

Example 1

A Technomelt PS 1540 resin (commercially available from Henkel AG & Co. KGaA; Tg: 2° C. to 4° C.) was melted at a temperature of 180° C. in an oil bath. Then, sodium carboxymethyl cellulose as an absorbent and zinc stearate (melt temp: 120° C. to 130° C.) as a fatty acid metal salt were sequentially added thereto, and mixed while stirring at a rate of approximately 100 rpm to prepare an adhesive for a stoma. In this case, the weight ratio of the solid content of the hot-melt resin, the solid content of sodium carboxymethyl cellulose, and the solid content of zinc stearate was 60:30:10.

After bubbles are removed from the adhesive for a stoma, the adhesive for a stoma was widely applied onto a surface of Kraft paper, and slowly cooled to prepare an adhesive layer specimen. Then, a release paper coated with silicone was stacked on the prepared adhesive layer specimen so that the release paper was attached to the adhesive layer specimen. Subsequently, the resulting adhesive layer specimen was interposed between stainless plates, and pressed under the conditions of a temperature of 55° C. to 65° C. and a pressure of 0.4 kgf/cm2 to 0.6 kgf/cm2 for 30 minutes. After releasing the pressure, the adhesive layer specimen was slowly cooled to prepare an adhesive tape for a stoma.

The adhesion of the adhesive tape for a stoma was measured according to ASTM D3330. Specifically, a specimen with a width of 25 mm×a width of 300 mm was applied to approximately 1,500 μm onto Kraft paper, and the 180° peel strength (N/25 mm) was measured at a temperature of 23 (±2)° C. and a rate of 300 mm/min using a tensile tester (an UTM 180° peel tester) to measure adhesion at room temperature. Also, the 180° peel strength (N/25 mm) was measured using the tensile tester to comparatively measure low temperature adhesion in a state in which the adhesive specimen was positioned for 10 minutes in a chamber atmosphere at a low temperature of 0° C.

The composition of the adhesive layer of Example 1 and the adhesion measurement results are listed in the following Table 1.

Example 2

An adhesive layer specimen was prepared in the same manner as in Example 1, except that iron (Fe) particles having an average particle size of 11.7 μm was mixed with the adhesive for a stoma, and the adhesion of the adhesive layer specimen was measured. In this case, the weight ratio of the solid content of the thermoplastic hot-melt resin, the solid content of sodium carboxymethyl cellulose, the solid content of zinc stearate, and the iron particles was 30:15:5:50.

The composition of the adhesive layer of Example 2 and the adhesion measurement results are listed in the following Table 1.

Comparative Example 1

An adhesive layer specimen was prepared in the same manner as in Example 1, except that the adhesive for a stoma was prepared using only the Technomelt PS 1540 resin, and the adhesion of the adhesive layer specimen was measured.

The composition of the adhesive layer of Comparative Example 1 and the adhesion measurement results are listed in the following Table 1.

Comparative Example 2

As another type of thermoplastic hot-melt resin, Kraton A1536 H (Tg: −25° C.), was melted at a temperature of 180° C. in an oil bath, and isobutylene rubber, rosin, P-3 oil as an emollient, and sodium carboxymethyl cellulose as an absorbent were sequentially added thereto, and mixed while stirring at a rate of approximately 100 rpm to prepare an adhesive for a stoma. In this case, the weight ratio of the solid content of the hot-melt resin, the solid content of isobutylene rubber, the solid content of rosin, the solid content of P-3 oil, and the solid content of sodium carboxymethyl cellulose was 42.9:7.9:17.5:15.9:15.7. Also, an adhesive layer specimen was prepared in the same manner as in Example 1, and the adhesion of the adhesive layer specimen was measured.

The composition of the adhesive layer of Comparative Example 2 and the adhesion measurement results are listed in the following Table 1.

TABLE 1

| | | Adhesion testing (ASTM D3330) | | | |
|---|---|---|---|---|---|
| | Main composition of adhesive (wt %) | Coating thickness (μm) | Room temperature adhesion N/25 mm (23 (±2)° C.) | Low temperature adhesion N/25 mm (0° C.) | Adhesion reduction rate (ΔF, %) |
| Example 1 | Technomelt PS 1540 (60), Zinc Stearate (10), Sodium Carboxymethyl Cellulose (30) | 1,500 | 24.0 | 2.8 | 88.3 |
| Example 2 | Technomelt PS 1540 (30), Zinc Stearate (5), Sodium Carboxymethyl Cellulose, (15) Fe powder (50) | 1,500 | 68.0 | 0.8 | 98.8 |
| Comparative Example 1 | Technomelt PS 1540 (100) | 1,500 | 75.2 | 70.1 | 6.8 |
| Comparative Example 2 | Kraton A1536 H (42.9), Isobutylene Rubber (7.9), Rosin (17.5), P-3 Oil (15.9), Sodium Carboxymethyl Cellulose (15.7) | 1,500 | 9.0 | 15.4 | −71.1 |

According to the results of Table 1, since the room temperature adhesion and the low temperature adhesion of the Comparative Example 1 to which 100 parts by weight of the Technomelt PS 1540 resin was applied were 75.2 N/25 mm and 70.1 N/25 mm, respectively, the adhesion reduction rate was merely 6.8%. On the other hand, it can be seen that, in the case of the adhesive obtained by mixing 42.9 parts by weight of another type of resin, Kraton A1536 H, as in Comparative Example 2 with 7.9 parts by weight of isobutylene rubber, 17.5 parts by weight of rosin, 15.9 parts by weight of P-3 oil, and 15.7 parts by weight of sodium carboxymethyl cellulose (based on solid content), as the room temperature adhesion and the low temperature adhesion were 9.0 N/25 mm and 15.4 N/25 mm, respectively, the low temperature adhesion rather increased by 71.1% compared to the room temperature adhesion. Therefore, it can be seen that the adhesives for a stoma according to Comparative Examples 1 and 2 to which the fatty acid metal salt was not applied had almost no adhesion reduction rate, or rather had increased adhesion at a low temperature.

On the contrary, it can be seen that both of Example 1 obtained by simultaneously mixing 10 parts by weight of zinc stearate and 30 parts by weight of sodium carboxymethyl cellulose with 60 parts by weight of the Technomelt PS 1540 resin, and Example 2 obtained by simultaneously mixing 5 parts by weight of zinc stearate, 15 parts by weight of sodium carboxymethyl cellulose, and 50 parts by weight of iron particles with 30 parts by weight of the Technomelt PS 1540 resin had a highly improved adhesion reduction rate, compared to Comparative Examples 1 and 2. In particular, it can be seen that the adhesion reduction rate was greater than 80% in the case of Example 1, and the adhesion reduction rate greatly exceeded 90% in the case of Example 2.

The results in which the low temperature adhesion in Examples 1 and 2 was greatly reduced compared to those of Comparative Examples 1 and 2 were thought to be due to the effect of zinc stearate, which is a fatty acid metal salt, added to the adhesive for a stoma. It was assumed that the zinc stearate included in the Technomelt PS 1540 resin having a glass transition temperature Tg of approximately 2° C. to 4° C. physicochemically reacted with a functional group (e.g., a carboxyl group, a ketone group, a hydroxyl group, and the like), which affected the adhesion of the resin, under a low temperature atmosphere to significantly reduce the adhesion of the adhesive layer. More specifically, it was assumed that the zinc stearate as a fatty acid metal salt in a cross-linked form formed in the Technomelt PS 1540 resin particularly served as a kind of thermal switch under the low temperature conditions to adaptively perform selective cross-linking in the resin.

In addition, it can also be seen that Example 2 to which 50 parts by weight of the iron particles were applied had lower low temperature adhesion compared to Example 1. It can be assumed that, when the iron particles had a high heat transfer rate, the adhesive for a stoma cohered well in a low temperature atmosphere. However, despite the performance benefits in the cooling function through such an excellent heat transfer rate, Example 1 may be more preferred when it is assumed that the cooling time at a low temperature is sufficient considering that the iron particles capable of hindering adhesion are added in Example 2.

The invention claimed is:

1. An adhesive for a stoma comprising:

a thermoplastic hot-melt resin; and a fatty acid metal salt, wherein the thermoplastic hot-melt resin is styrene-based hot-melt resin having a glass transition temperature of −10° C. to 30° C., wherein the content of the fatty acid metal salt is 10 parts by weight or more and 30 parts by weight or less, based on 100 parts by weight of the thermoplastic hot-melt resin, and wherein the adhesion reduction rate ΔF defined by the following General Formula 1 is at least 50%:

$$\Delta F = \frac{(\text{Room-temperature adhesion} - \text{Low-temperature adhesion})}{\text{Room-temperature adhesion}} \times 100 \quad \text{[General Formula 1]}$$

wherein:

the room temperature adhesion is a value measured at 23° C. according to ASTM D3330, and the low temperature adhesion is a value measured at 0° C. according to ASTM D3330.

2. The adhesive of claim 1, wherein the fatty acid metal salt is dispersed in a polymeric matrix derived from the thermoplastic hot-melt resin.

3. The adhesive of claim 1, wherein the fatty acid metal salt is derived from a fatty acid selected from caprylic acid ($C_8H_{16}O_2$), lauric acid ($C_{12}H_{24}O_2$), myristic acid ($C_{14}H_{28}O_2$), palmitic acid ($C_{16}H_{32}O_2$), stearic acid ($C_{18}H_{36}O_2$), linolenic acid ($C_{18}H_{30}O_2$), arachidonic acid ($C_{20}H_{32}O_2$), oleic acid ($C_{18}H_{34}O_2$); and a metal selected from lithium (Li), aluminum (Al), calcium (Ca), magnesium (Mg), potassium (K), zinc (Zn), and sodium (Na).

4. The adhesive of claim 1, wherein the adhesive for a stoma further comprises at least one heat transfer particle selected from the group consisting of metal particles, ceramic particles, and carbon particles.

5. The adhesive of claim 4, wherein the content of the heat transfer particles is 10 parts by weight to 200 parts by weight, based on 100 parts by weight of the thermoplastic hot-melt resin.

6. The adhesive of claim 1, further comprising one or more additives selected from the group consisting of a coagulant, a tackifier, an antioxidant, a dispersion stabilizing agent, a coupling agent, a thickening agent, and a drying control agent.

7. The adhesive of claim 1, wherein the adhesive for a stoma has a room temperature adhesion of at least 10 N/25 mm.

8. The adhesive of claim 1, wherein the adhesion reduction rate is at least 80%.

9. An adhesive tape for a stoma comprising a base layer; and an adhesive layer provided on one surface of the base layer, wherein the adhesive layer comprises the adhesive for a stoma according to claim 1.

10. The adhesive tape of claim 9, wherein the base layer further comprises at least one heat transfer particle selected from the group consisting of metal particles, ceramic particles, and carbon particles.

* * * * *